United States Patent
Huang et al.

(10) Patent No.: US 7,255,687 B2
(45) Date of Patent: Aug. 14, 2007

(54) SYSTEMS AND METHODS FOR LUMINAL ACCESS

(75) Inventors: Alexander L. Huang, Menlo Park, CA (US); Kenneth A. Peartree, Redwood City, CA (US); Henry Lao, Sunnyvale, CA (US)

(73) Assignee: Percutaneous Systems, Inc., Mountain View, CA (US)

( * ) Notice: Subject to any disclaimer, the term of this patent is extended or adjusted under 35 U.S.C. 154(b) by 119 days.

(21) Appl. No.: 10/993,631

(22) Filed: Nov. 19, 2004

(65) Prior Publication Data

US 2006/0122566 A1   Jun. 8, 2006

(51) Int. Cl.
*A61M 5/00* (2006.01)

(52) U.S. Cl. .................................... 604/271

(58) Field of Classification Search ............. 604/271, 604/103.1, 525–526
See application file for complete search history.

(56) References Cited

U.S. PATENT DOCUMENTS

| | | | |
|---|---|---|---|
| 3,168,092 A | 2/1965 | Silverman | |
| 3,421,509 A | 1/1969 | Fiore | |
| 3,589,356 A | 6/1971 | Silverman | |
| 4,043,345 A | 8/1977 | Kramann et al. | |
| 4,863,440 A * | 9/1989 | Chin | 604/271 |
| 5,458,573 A * | 10/1995 | Summers | 604/101.04 |
| 5,531,717 A | 7/1996 | Roberto et al. | |
| 5,676,688 A | 10/1997 | Jaker et al. | |
| 5,711,841 A | 1/1998 | Jaker | |
| 5,792,114 A | 8/1998 | Fiore | |
| 5,897,535 A | 4/1999 | Feliziani et al. | |
| 6,007,488 A | 12/1999 | Jaker et al. | |
| 6,007,521 A | 12/1999 | Bidwell et al. | |
| 6,200,968 B1 | 3/2001 | Dickason et al. | |
| 6,217,569 B1 | 4/2001 | Fiore | |
| 6,485,409 B1 | 11/2002 | Voloshin et al. | |
| 6,585,721 B2 | 7/2003 | Fiore | |
| 6,908,428 B2 | 6/2005 | Aizenfeld et al. | |
| 6,988,988 B2 | 1/2006 | Voloshin et al. | |
| 2001/0044595 A1 * | 11/2001 | Reydel et al. | 604/98.02 |

FOREIGN PATENT DOCUMENTS

EP          605427 B1       7/1994

* cited by examiner

*Primary Examiner*—Catherine S. Williams
(74) *Attorney, Agent, or Firm*—Townsend and Townsend and Crew LLP

(57) ABSTRACT

A luminal access system comprises an evertable, lubricious sleeve, a pusher tube, and optionally a lumen tube. The evertable, lubricious sleeve is attached to a non-evertable sheath which is coaxially received over the pusher tube. A distal portion of the evertable sleeve folds or everts into an axial passage of the pusher tube where it is connected to a lumen tube. A distal portion of the pusher tube may be bendable, typically comprising a relatively soft polymer which is circumferentially reinforced to enhance hoop strength.

17 Claims, 6 Drawing Sheets

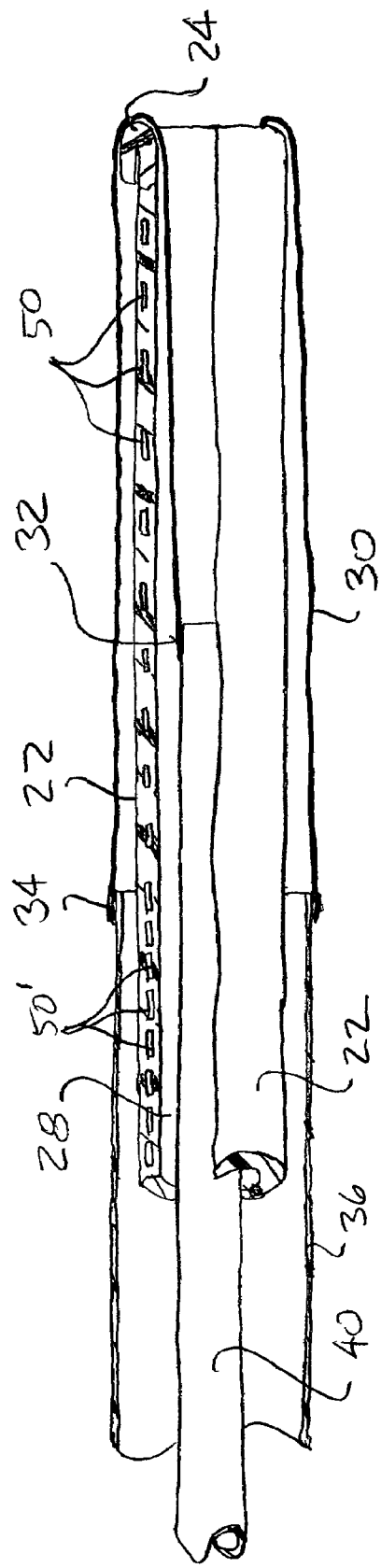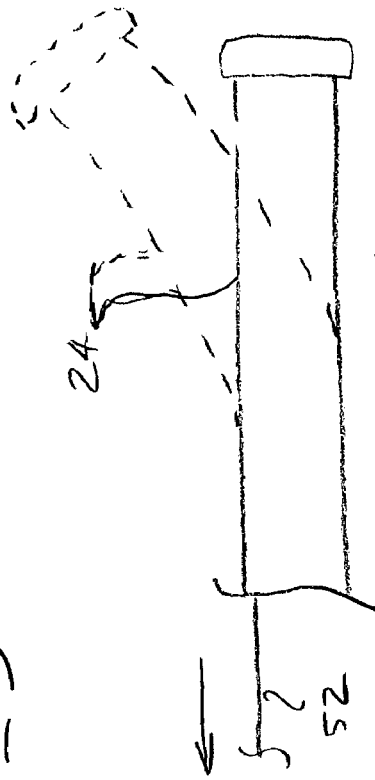

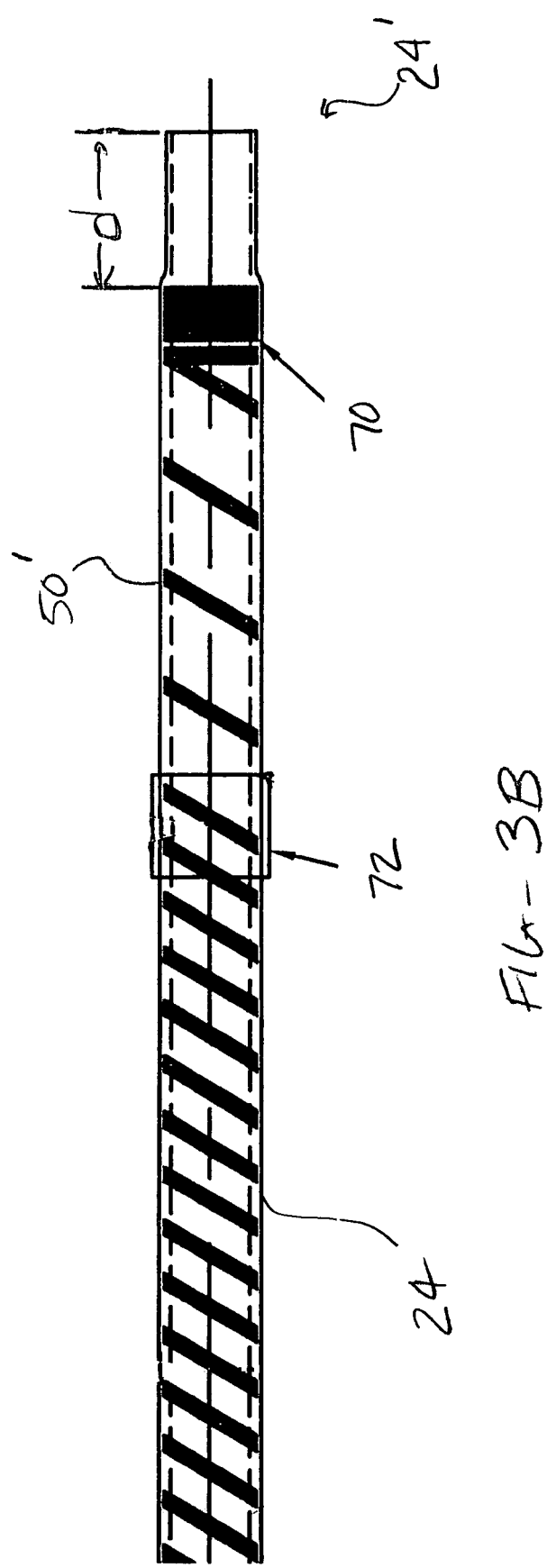

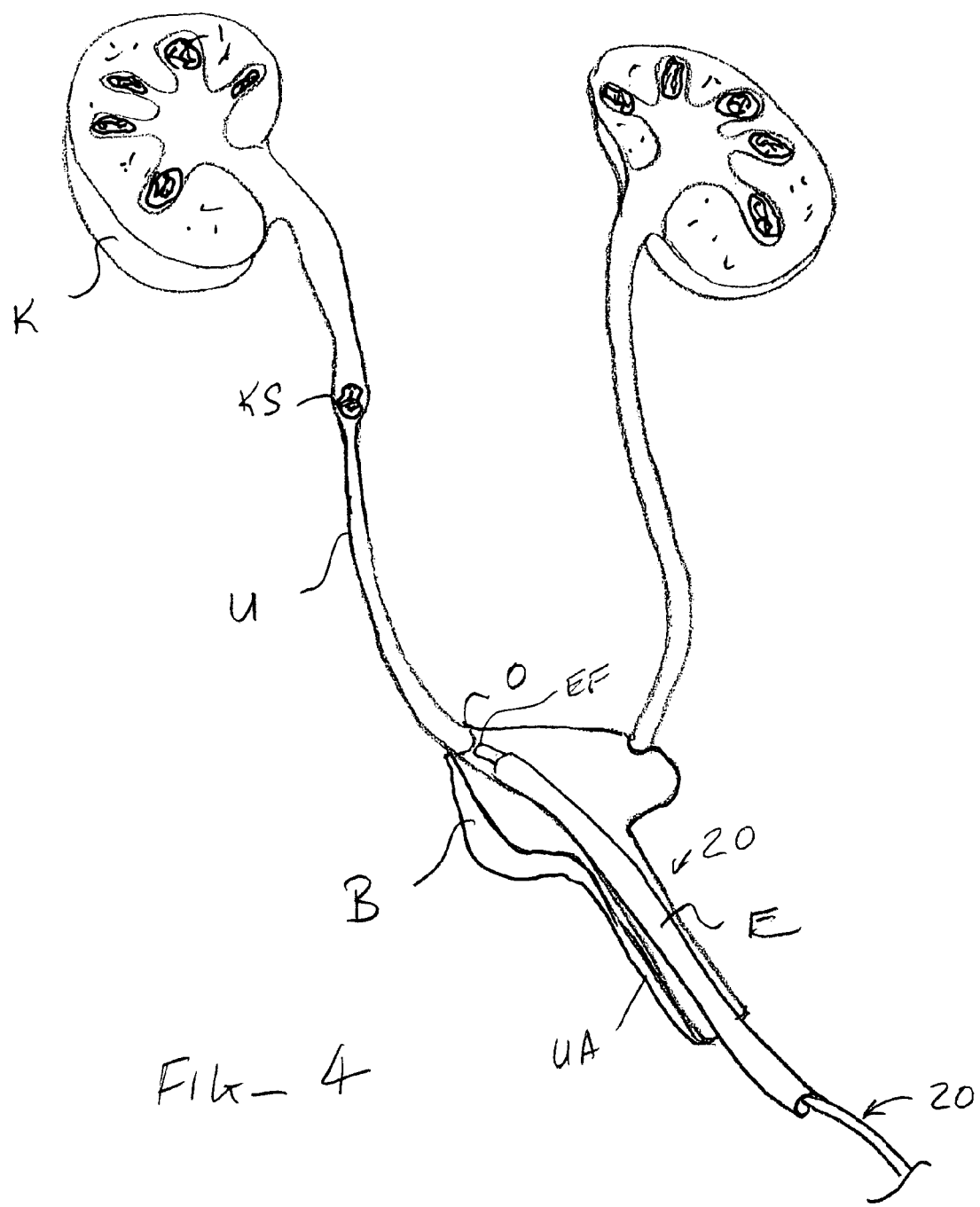

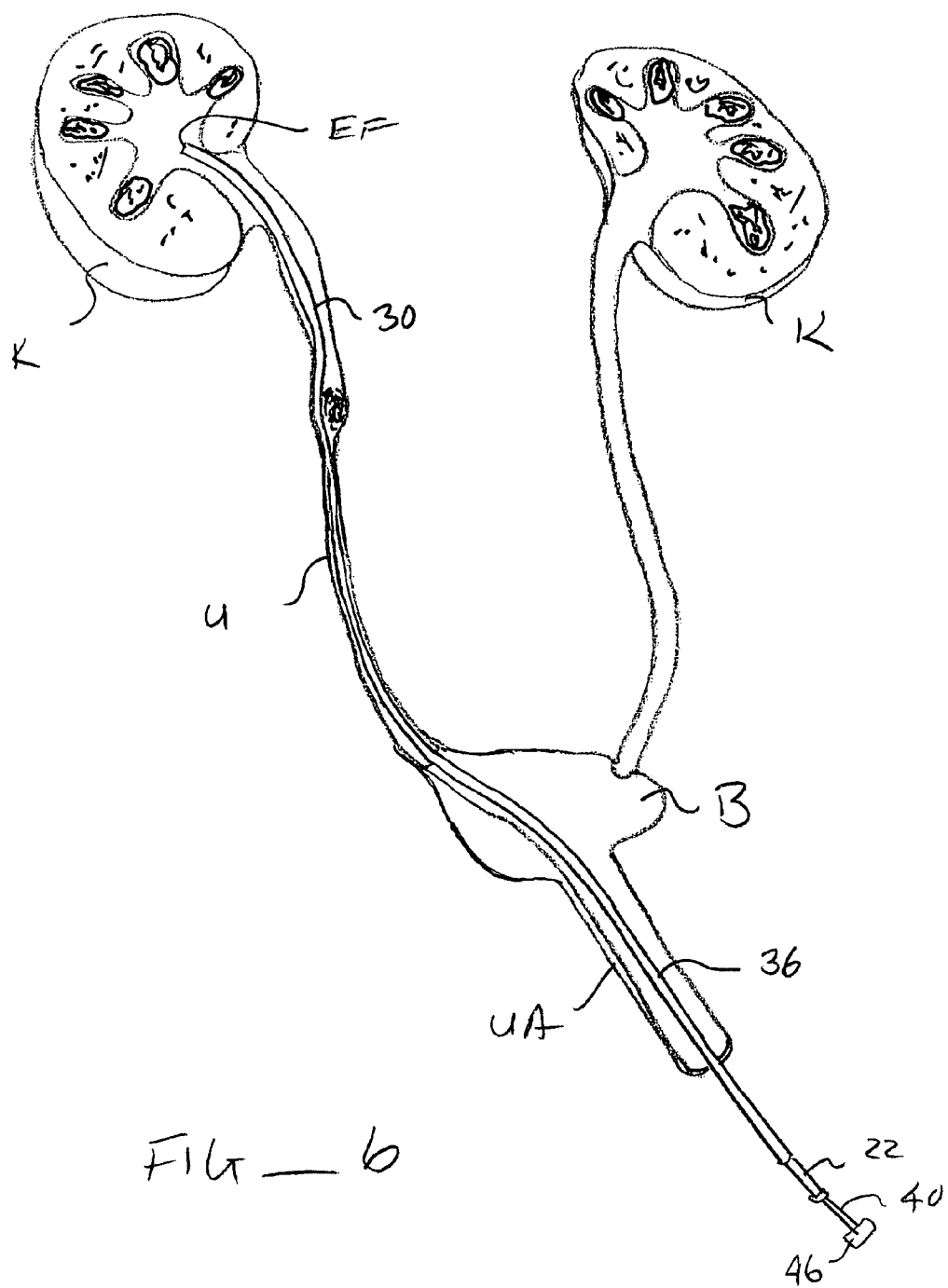
FIG — 6

SYSTEMS AND METHODS FOR LUMINAL ACCESS

BACKGROUND OF THE INVENTION

1. Field of the Invention

The present invention relates generally to medical apparatus and methods for using such apparatus. In particular, the present invention relates to systems and methods for accessing target locations in or through natural and created body lumens.

A wide variety of catheters and probes are used in an almost unlimited number of medical procedures and protocols. Of particular interest herein, tubular catheters are often used to provide access through body lumens, for example, through a patient's urethral canal to permit draining the bladder. Such catheters are typically referred to as urinary catheters and are inserted into the bladder via the urethra. Ureteral catheters can be inserted into the ureter via the bladder to reach the kidneys. The catheters can have a variety of purposes, including access to/capture of and/or destruction of urinary calculi. The introduction of such urinary and uretal catheters is often the cause of urinary infections. For example, the introduction of urinary catheters into the urethra can carry bacteria or other infections materials from the patient's skin or the lower urinary tract into the bladder or from the bladder into the upper urinary tract. The leading tip of such conventional catheters can act as a pusher or transfer device that can unintentionally spread infection.

Even if proper precautions are taken to reduce or eliminate infection, the advancement of conventional catheters through the urethra, ureter, or other small body lumens can irritate the luminal wall and cause discomfort or, in the worst cases, injury to the walls. Even if no serious damage is caused, the resulting scarring can lead to stricture formation and discomfort can be substantial.

To overcome both of these problems, RTC, Inc. of St. Paul, Minn., has developed the Memcath™ Intermittent Urology Catheter which uses a PTFE sheath which everts from the interior of the catheter over the exterior as the catheter is introduced. As illustrated in FIG. 1, the Memcath™ catheter 10 has a tubular PTFE membrane 12 which is initially stowed within the lumen 14 of the catheter. The membrane extends out a distal end of the catheter 10 and has an everting section 18 which attaches to a ring 20 which can slide over the exterior surface of the catheter. In this way, as the catheter 10 is advanced into a body lumen, such as the urethra, the tubular membrane 10 will be pulled around the distal end 16 of the catheter to cover the exterior of the catheter as it advances. Since the ring 20 is held stationary relative to the body lumen, the membrane, once it is deployed, will also remain stationary, reducing the risk of trauma to the luminal wall and preventing the propagation of bacteria and other pathogens upward into the body lumen.

While this design is fundamentally sound, it does suffer from certain shortcomings. The ring 20 is intended to be held manually over the access orifice of the body lumen. Thus, the Memcath™ catheter is suitable for introduction through the urethra, but would be difficult to deploy in the ureter or other internal body lumen, particularly using an endoscope or other minimally invasive approach. The distal end of the catheter 10 is relatively stiff, so introduction of the catheter through a relatively tortuous path and/or past obstructing material, such as urinary calculi, can be difficult. Additionally, if the membrane 12 is not fully deployed, a trailing end can remain within the lumen 14 of the catheter, making access through the lumen difficult.

For these reasons, it would be desirable to provide improved designs and methods of use for luminal access catheters of the type which include a protective, deployable outer membrane. In particular, it would be desirable to provide such catheters which are suitable for endoscopic and other minimally invasive deployments. It would further be desirable to provide such catheters having relatively flexible or deflectable distal ends to permit introduction into relatively tortuous lumens and/or introduction past obstructing materials within such lumens. It would further be desirable if the catheters were suitable for introduction over guidewires in at least some circumstances. Additionally, it would be desirable to provide such catheters which maintain an open lumen, even if the protective sheath is not fully deployed while the catheter is introduced. It would be further desirable if the membrane position could be reset after use to allow multiple advancements with the same catheter in a single patient. At least some of these objectives will be met by the inventions described below.

2. Description of the Background Art

The use of an everting sleeve composed of thin, tensilized polytetrafluoroethylene for introducing catheters to body lumens is described in U.S. Pat. Nos. 5,531,717; 5,676,688; 5,711,841; 5,897,535; 6,007,488; 6,240,968; and EP605427B1. Other catheters employing everting sleeves for a variety of purposes are described in commonly assigned, copending application Ser. Nos. 10/794,337, filed on Mar. 5, 2004, Ser. No. 10/794,317, filed on Mar. 5, 2004, and Ser. No. 10/886,886, filed on Jul. 7, 2004, the full disclosures of which are incorporated herein by reference.

BRIEF SUMMARY OF THE INVENTION

The present invention provides systems and methods for accessing target locations within a patient's body. The target locations will often be inside of a body cavity, organ, or body lumen, but can also be within solid tissue. Typical target locations include those intended for therapy, such as drainage, drug delivery, ablation, excision, thermal treatment, photodynamic therapy, and the like. Exemplary therapeutic treatments include drainage of the bladder through the urethra and treatment of the kidneys through the ureter. The present invention is particularly suitable for endoscopic deployment of a drainage catheter into the kidneys through the ureter. Alternatively, the target locations accessed using the present invention may be intended for diagnosis, including biopsy, aspiration, imaging, chemical analysis, and the like.

In either case, the target location will usually be reached at least partly through a natural body lumen, such as a urethra, a ureter, a blood vessel, a hepatic duct, a cystic duct, a cervical canal, a fallopian tube, or the like. The access system can be advanced or deployed to a site adjacent to the natural body lumen in a minimally invasive manner, typically using an endoscope, a cystoscope, a thoracoscope, or other percutaneous device. Less commonly, the present invention could be used to provide access through solid tissue, particularly non-fibrous tissue such as brain tissue, or between adjacent tissue planes or layers. For access through solid tissue, it will usually be necessary to form a tissue tract either before or at the same time as introducing the access system of the present invention.

An exemplary technique employing the access system of the present invention will be described in connection with transuretal access to the kidneys where the system is first introduced to the bladder using an endoscope. It will be appreciated, however, that the principles of the embodiments of the present invention may be applied to a much wider variety of target locations and access routes.

In a first aspect, the present invention provides a luminal access system comprising an evertable, lubricious sleeve and a pusher tube. The pusher tube has a distal end, a proximal end, and an axial passage between the distal and proximal ends. The sleeve is stowed within the axial passage of the pusher tube and is able to evert over the distal end of the tube. It can thereby extend over the exterior of the tube to provide a protective interface as the tube is advanced through a body lumen. In some embodiments, the distal end of the pusher tube may be steerable, e.g., being flexibly curved or shaped or having pull wire(s) or other mechanisms for selectively deforming the distal end to permit steering of the access system through a branching luminal network such as the vasculature. The evertable, lubricious sleeve and the pusher tube are common system components to several different embodiments of the present invention, each of which will be described in more detail below.

In a first embodiment of the luminal access system, the pusher tube is characterized by a distal portion which is circumferentially reinforced, for example to enhance hoop strength, while at the same time being relatively more bendable than a proximal portion of the pusher tube. The relatively bendable distal portion of the pusher tube has a number of advantages. First, it allows the pusher tube to be advanced through body lumens which are more tortuous than would be accessible with the Memcath™ catheter or many other luminal access catheters of the prior art. Second, the bendability and enhanced flexibility of the distal portion will allow the pusher tube to be advanced past potential luminal obstructions in the body lumen being accessed with less risk of lumen penetration. For example, when advancing the pusher tube through a ureter, the pusher tube will be able to more easily pass by urinary calculi which might block the lumen. Third, the bendable distal end will allow the device to track over a guidewire through tortuous lumens should this be desired. Fourth, the bendable section can be combined with a pull wire to permit selective deflection and steering of the tube in the body lumen.

Typically, the pusher tube will comprise a polymeric tube, at least over its distal portions. The polymer may be selected from a variety of suitable polymers, including polyethylenes, polyurethane(s), polyolefins, EVA, Pebax, and the like. In the exemplary embodiment, the distal portion of the pusher tube will typically comprise a composite of two or more of these polymers while the proximal portion of the pusher tube will comprise a high density polyethylene or polyimide. The distal portion of the pusher tube will usually be circumferentially reinforced, typically by a coil structure, more typically a ribbon wire coil, where the pitch varies to control stiffness and bendability along the distal length. An exemplary reinforcement ribbon will be composed of stainless steel, nickel-titanium alloy, or other suitable metal, and will have a width in range from 0.1 mm to 1 mm, a thickness in the range from 0.003 mm to 0.4 mm, and a spacing between adjacent turns that varies in the range from 0.2 mm to 2 mm. It will be appreciated, however, that other circumferential reinforcement structures could be utilized, including axially spaced apart hoops, braids, disks, or the like. Whatever reinforced structure is chosen, however, it is desirable that the bendability of the distal portion not be compromised to limit the ability of the pusher tube to traverse tortuous body lumens, be advanced past luminal obstructions, and the like.

The evertable, lubricious sleeves are typically polymeric tubes, particularly thin-walled polymeric tubes made from a lubricious polymer or a polymer which may be lubricated on at least one side. The polymeric tube typically has a length in the range from 5 cm to 90 cm, preferably from 10 cm to 35 cm, an inner diameter (for a single lumen) in the range from 2 mm to 12 mm, preferably in the range from 2 mm to 6 mm, and a wall thickness in the range from 0.01 mm to 0.05 mm, preferably from 0.02 mm to 0.04 mm. Exemplary polymers for the polymeric tube include polytetrafluoroethylene (PTFE), polyethylene (PE), perfluoroalkoxy (PFA), polyurethane (PU), perfluoromethylvinylether (MFA), perfluoropropylvinylether (PPVE), and copolymers thereof. Preferred polymers include tensilized PTFE/PPVE copolymers.

In a second embodiment of the present invention, the evertable, lubricious sleeve may be attached to or formed as part of an outer sheath structure typically comprising a relatively stiff and non-evertable tube. The tube will be disposed coaxially over the pusher tube and have a distal end extending from "an outside" end of the evertable, lubricious sleeve, i.e., the end which is positioned to move over the outside of the pusher tube. Prior to deployment, the "outside end" of the lubricious sleeve will be positioned at or near the distal end of the pusher tube. During deployment, the outside end will remain generally stationary relative to the body lumen as the distal end of the pusher tube is advanced distally relative to the body lumen to evert and advance a leading fold of the sleeve over the distal end of the pusher tube.

The non-evertable sheath, prior to deployment of the sleeve, will typically cover most of the pusher tube and allow the user to position, hold, or otherwise manipulate the system prior to advancement of the pusher tube. The non-evertable sheath is advantageous since, for example, it can be used to advance the luminal access system of the present invention through an endoscope. Once the system is in place, the sheath can be held relative to the endoscope to immobilize the proximal end of the lubricious sleeve as the pusher tube is advanced relative to the body lumen. Thus, in at least one aspect, the non-evertable portion of the sheath serves to replace the anchor ring 20 of the prior art Memcath™ catheter illustrated in FIG. 1. Alternatively, the user could selectively reposition the proximal end of the lubricious sleeve using the non-everting sheath should it be desirable for any reason to do so.

Typically, the non-evertable sheath will comprise a flexible polymeric tube. The flexible tube usually has a length in the range from 5 cm to 50 cm, an inner diameter in the range from 1 mm to 12 mm, and a wall thickness in the range from 0.01 mm to 0.1 mm. Suitable polymers include polyimide, Pebax, polyethylene, fluoropolymers, and the like.

In a third embodiment of the luminal access system of the present invention, the system further comprises a lumen tube having a distal end, a proximal end, and a central passage between the distal end and the proximal end. The lumen tube will be positionable within the axial passage of the pusher tube and will be attached at its distal end to the "inner end" of the lubricious sleeve, i.e., the end positioned within the central passage of the pusher tube. Thus, the lumen tube will be attached at the end of the lubricious sleeve which is generally located or stowed within the axial passage of the pusher tube. The other or "outer end" of the lubricious sleeve will typically be attached to the non-evertable sheath as discussed above. The lumen tube will extend generally in a proximal direction from the sleeve, that is in a direction toward the proximal end of the pusher tube. The lumen tube will be able to slide freely within the axial passage of the pusher tube and will typically be advanced distally relative to the pusher tube as the pusher tube is advanced distally within the body lumen. That is, the lumen tube will move in unison and synchrony with the inner end of the lubricious sleeve to which it is attached. Conversely, pulling proximally on the lumen tube can pull back or reverse deployment of the sleeve in the body lumen. Thus, the preferred embodiments of the present invention which comprise both the non-evertable sheath and the lumen tube allow for bidirectional deployment and positioning of the access system.

The lumen tube will typically be composed of a polymer, such as polyethylene, Pebax, polyimide, fluoropolymers, and the like. The lumen tube typically will have a length sufficient with the pusher tube fully extended to provide luminal access for the insertion or manipulation of various devices, such as guidewires, wire baskets, lithotripters, and the like. The lumen tube may have a luer or other conventional medical fitting on its proximal end to allow connection of the lumen tube to an aspiration source, infusion source, or other therapeutic or diagnostic system.

The lumen tube is beneficial since it improves access through the pusher tube of the luminal access system. It will be appreciated that without the lumen tube, access would have to be made directly through the axial passage of the pusher tube. In many cases, such access may be sufficient. In other instances, for example when a portion of the lubricious sleeve remains within the axial passage of the pusher tube, such access may be compromised. Use of the lumen tube which is directly connected to the inner end of the lubricious sleeve, however, assures that access through the pusher tube can be easily effected regardless of the position of the lubricious sleeve.

It will be appreciated that each of the embodiments of the present invention just described may be employed individually or in combination with each other. In the exemplary embodiments, the luminal access system which is illustrated will combine each of the bendable distal end of the pusher tube, non-evertable proximal sheath portion, and lumen tube. Each of these aspects of the present invention, however, are considered to define separate inventions.

In a second aspect of the present invention, methods for accessing a body lumen comprise disposing an everted edge of a lubricious sleeve adjacent to an access point on a body lumen, typically a natural body orifice, an incision to access a body lumen, or a tissue tract formed through tissue to the body lumen. A pusher tube, optionally having a bendable distal end, is distally advanced against a proximal side of the everted edge to distally advance the everted edge into the body lumen. An outer end of the sleeve is immobilized relative to the pusher tube, and a lumen tube is drawn into the body lumen by an inner end of the sleeve.

In preferred aspects of the method, the outer end of the sleeve is immobilized using a sheath tube secured to said outer end. As described above in connection with the systems of the present invention, the sheath may conveniently be a non-everting tube connected to or an extension of the lubricious sleeve. The pusher tube may be advanced through tortuous lumens, optionally being advanced over a guidewire disposed in the body lumen. In such cases, the distal portion of the pusher tube is typically conformable to track through the lumen or over the guidewire and the proximal portion of the pusher tube has sufficient column strength to push the distal portion in the distal direction. Once in place, a material or instrument may be introduced through the passage of the lumen tube and out of the distal end of the pusher tube. Optionally, the lubricious sleeve may be positioned in advance through an endoscope or other access cannula prior to advancing the pusher tube into the body lumen. The body lumen is typically a natural body lumen, such as a urethra, a ureter, a blood vessel, a hepatic duct, a cystic duct, a cervical canal, a fallopian tube, or the like.

A particular advantage of the present invention is the ability to reverse deployment of the lubricious sleeve at any time during a procedure by pulling proximally the inner end of the sleeve, typically via the attached lumen tube. Pulling on the lumen tube will cause the previously deployed sleeve to be pulled from the adjacent tissue back into the axial passage of the pusher tube. In this way, trauma to the luminal wall resulting from withdrawal of the system is reduced and the risk of transport of pathogens, tumor cells, cellular debris, and other potential contaminants along the lumen is lessened.

BRIEF DESCRIPTION OF THE DRAWINGS

FIG. 3 is a detailed view of the distal end of the luminal access system of FIG. 2, shown in partial section.

FIG. 3A is a detailed view of the distal end shown with a pull wire useful for steering.

FIG. 3B is a detailed view of the distal end of the pusher tube.

FIGS. 4-6 illustrate use of the luminal access system of FIGS. 2 and 3 for accessing a kidney using endoscopic deployment through the bladder.

DETAILED DESCRIPTION OF THE INVENTION

The systems and methods of the present invention are useful for providing access through any natural or created body lumen of a patient where it is desired to temporarily or permanently place an access tube or a structure. Most commonly, the systems and methods will be used to place a drainage, infusion, or other interventional tube or instrument through a natural body lumen to a target site within the body lumen or a hollow body organ connected to the natural body lumen. The methods described in the following description are directed specifically at accessing a kidney through a ureter where the access system of the present invention has been deployed through an endoscope passed through the urethra. It will be appreciated, however, that the principles of the present invention will apply more broadly as discussed above.

Figure 1:
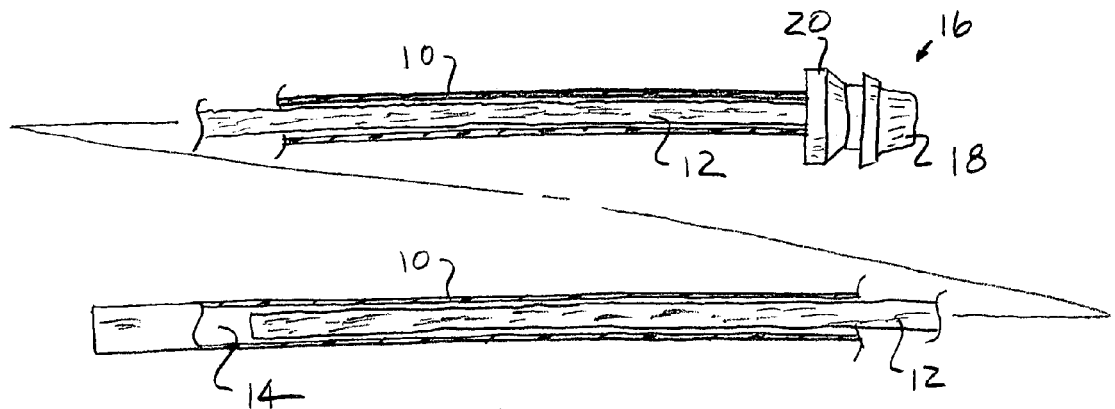
FIG. 1 illustrates a Memcath™ luminal access catheter of the prior art.
Figure 2:
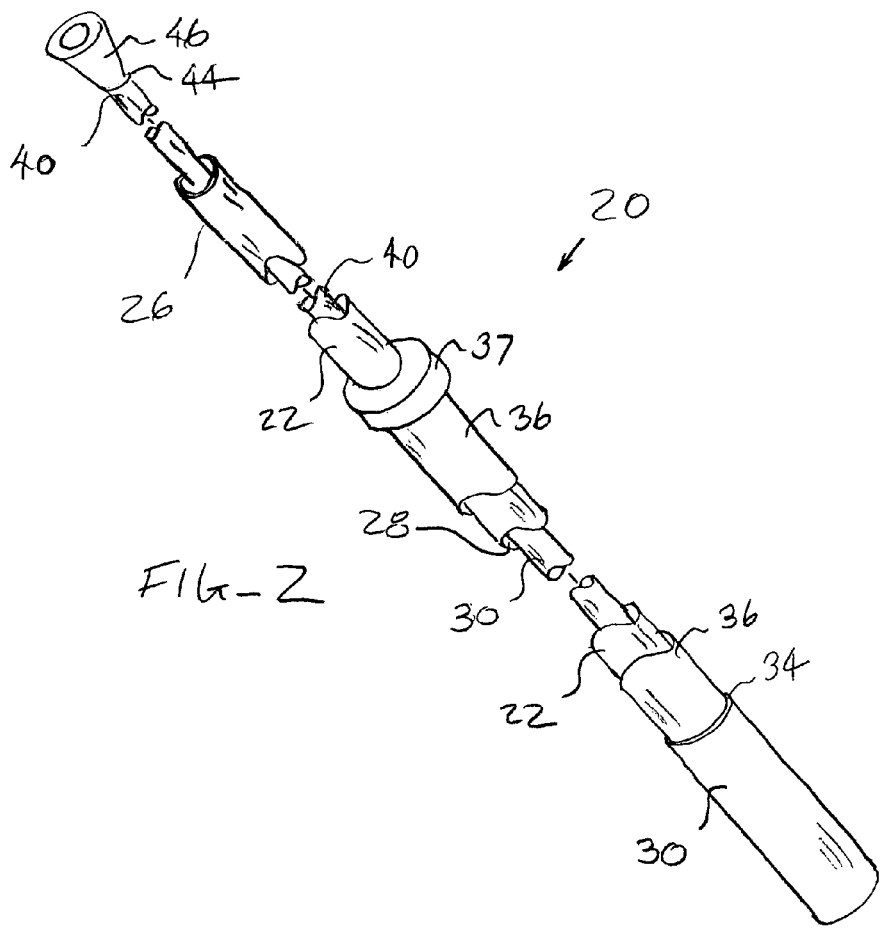
FIG. 2 is a perspective view of a luminal access system constructed in accordance with the principles of the present invention shown with portions broken away.

Referring now to FIGS. 2 and 3, an exemplary luminal access system 20 constructed in accordance with the principles of the present invention comprises a pusher tube 22 having a distal end 24, a proximal end 26, and an axial passage 28 extending from the proximal end to the distal end. An evertable, lubricious sleeve 30 everts or folds back over the distal end 24 of the pusher tube 22 so that an inner end 32 of the sleeve is located within the lumen or axial passage 28 of the pusher tube 22 and an outer end 34 is located over the exterior of the pusher tube.

The outer end 34 of the sleeve 30 is attached to a sheath 36 which is typically non-evertable (i.e., having sufficient stiffness to allow the user to manipulate the sleeve from the proximal end and is coaxially received over the exterior of the pusher tube 22. As described above, both the evertable, lubricious sleeve 30 and the sheath 36 will usually be composed of polymers, and the attachment at outer end 34 can be made in any manner suitable for attaching the polymers, e.g., by heat welding, the use of adhesives, sonic welding, the use of staples or other fasteners, or the like. A hub 37 may be at the proximal end of the sheath 36 to provide a sliding seal against the pusher tube 22.

A lumen tube 40 is coaxially received within the axial passage 28 of the pusher tube 22. The distal end 32 of lubricious sleeve 30 is attached to the distal end of the lumen tube 40, as best seen in FIG. 3. A luer or other attachment fitting 46 may be provided on a proximal end 44 of the lumen tube 40, and a proximal portion of the lumen tube will typically pass out of the pusher tube 22 as shown in FIG. 2.

In a preferred aspect of the present invention, the pusher tube 22 will be reinforced, at least over a distal portion thereof. As shown in FIG. 3, the distal portion is reinforced by a flat ribbon wire coil 50 comprising adjacent turns which are spaced apart by a distance which is greater than the width of the wire. In this way, the distal portion of the pusher tube is radially reinforced to provide hoop strength while remaining sufficiently bendable to pass through relatively tortuous body lumens and bypass obstructions within the body lumens. To achieve such a flexibility, at least the distal portion of the pusher tube will typically be composed of a relatively soft polymer, such as low density polyethylene (LDPE). Optionally, a pull wire 52 or other steering mechanism may be provided to deflect the tip 24, as shown in broken line, to facilitate advancement.

The proximal portion of the pusher tube will generally be less bendable and therefore more pushable than the distal section just described. The proximal portion will typically be composed of a stiffer polymer, such as high density polyethylene (HDPE) and may optionally be reinforced using a flat or circular coil, braiding, hoop structures, or the like. As illustrated in FIG. 3, reinforcement of the proximal end comprises the same wired coil used to reinforce the distal end, where the adjacent turns of the wire coil 50' are spaced together much more closely than in the distal portion. Such close spacing enhances not only the hoop strength but also the column strength of the distal portion of the pusher tube. The relative lengths of the distal portion and the proximal portion may vary greatly. Typically, the relatively bendable distal portion of the pusher tube will have a length in the range from 0.5 cm to 4 cm while the relatively more pushable proximal section of the pusher tube will have a length in the range from 4 cm to 90 cm.

As a further optional feature, the distal end 24 of the pusher tube may be configured to enhance lubricity and/or hoop strength. As the lubricious sleeve 30 will be everted over the distal end 24, it is desirable that the friction between the sleeve and the distal end be minimized. The preferred materials of the lubricious sleeve, as described above, are inherently lubricious. Optionally, friction may be further reduced by enhancing the lubricity of the distal end 24. This may be done by selecting the proper materials, and/or lubricants, and/or tip profile for the distal-most end.

A specific distal tip configuration 24' is illustrated in FIG. 3B. The pusher tube 24 terminates in a short section (d=1.5 mm) of high lubricity LDPE with the distal end folded back and heat set as shown on FIG. 3. The remaining length of the tube 24 may be composed of LDPE with a higher coefficient of friction. A ring 70 of radiopaque material, such as gold or platinum, is positioned between the tip 24' and the beginning of the wire coil 50'. The ring serves both as a radiopaque marker and as a termination point for the coil. A reinforcement sleeve 72 is provided over the transition point between the high pitch and low pitch sections of the reinforcing coil.

Figure 5:
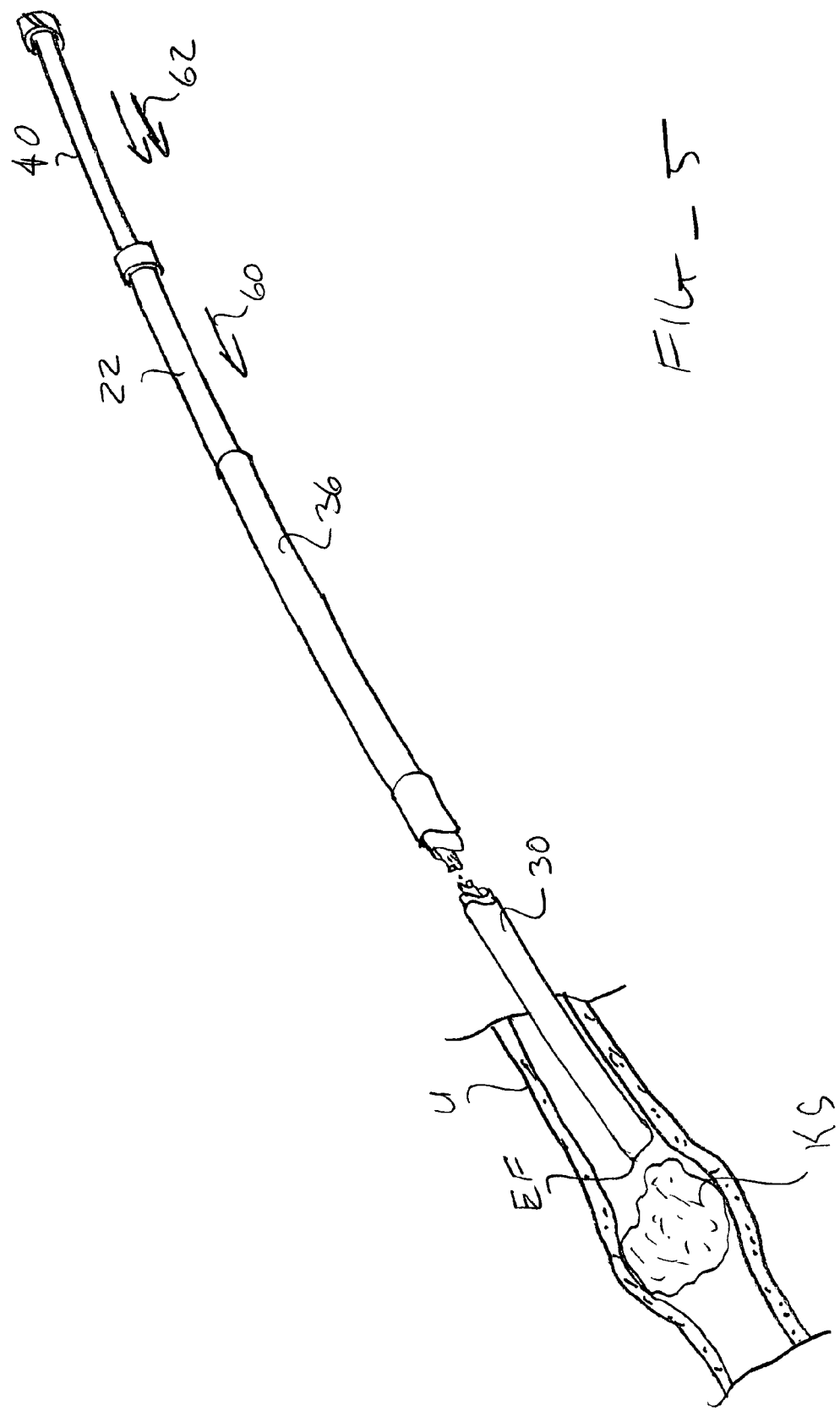

Referring now to FIGS. 4-6, use of the luminal access system 20 for accessing a kidney K will be described. As illustrated in FIG. 4, the kidney K is located at the end of the patient's ureter U which extends between the kidney and the patient's bladder B. The luminal access system may be deployed through an access cannula, typically within an endoscope E, passed through the patient's urethra UA. The distal end of the pusher tube is then used to advance the everting fold EF of the access system through the ureter optionally under imaging if an endoscope is being used to provide an access cannula.

As shown in FIG. 5, the everting fold EF of the lubricious sleeve 30 is advanced by pushing the proximal portion of the pusher tube 22 forwardly in the direction of arrow 60 into sheath 36. The proximal portion of the pusher tube 22 will remain outside the patient and available for manual advancement by the physician. Typically, the physician will hold a proximal portion of the sheath 36 which will in turn immobilize the already deployed portion of the lubricious sleeve 30 within the ureter U. As the pusher tube 22 is manually advanced, the sleeve 30 is pulled from the passage of the pusher tube 22. Lumen tube 40 will be carried distally in the direction of arrow 62 as its distal end is dragged by the distal end 32 of the sleeve 30. Because the distal end 24 of the pusher tube acts like a pulley, sleeve material is pulled from the central passage of the pusher tube 22 at a rate which is twice as fast as the rate at which the pusher tube 22 is being manually advanced. Thus, the lumen tube 40 will advance at a rate twice as fast as the pusher tube 20 is being advanced.

As shown in FIG. 5, the everting fold EF of the sleeve 30 has just reached an occluding structure within the ureter, typically a kidney stone KS. The bendable proximal portion of the pusher tube is advantageous in that it facilitates bypass of the kidney stone by the luminal access system as it is advanced.

As shown in FIG. 6, the pusher tube 22 can continue to be advanced until the everting fold EF has reached the interior of the kidney. The luer fitting 46 of the lumen tube 40 is then available for connection to a drainage source, infusion source, or other therapeutic or diagnostic apparatus, where it is desired to be connected to the interior of the kidney K.

What is claimed is:

1. A method for accessing a body lumen, said method comprising:
    disposing an everted edge of a lubricious sleeve adjacent to an access point on the body lumen; and
    distally advancing a pusher tube against a proximal side of the everted edge to distally advance the everted edge into the body lumen, wherein an outer proximal end of the sleeve is immobilized relative to the pusher tube, and wherein a lumen tube is attached to an inner distal end of the sleeve and is drawn into the body lumen by the inner distal end of the sleeve;
    wherein the lubricious sleeve is positioned through an endoscope prior to advancing the pusher tube.

2. A method as in claim 1, further comprising immobilizing the outer proximal end of the sleeve using a sheath tube secured to said outer proximal end.

3. A method as in claim 1, wherein the pusher tube is advanced over a guidewire disposed in the body lumen.

4. A method as in claim 3, wherein a distal portion of the pusher tube is conformable to track the guidewire and a proximal portion of the pusher tube has sufficient column strength to push the distal portion over the guidewire.

5. A method as in claim 1, further comprising introducing or removing a material or instrument through a lumen of the lumen tube.

6. A method as in claim 1, wherein the lubricious sleeve is initially disposed in an axial passage of the pusher tube and the pusher tube.

7. A method as in claim 6, wherein the lubricious sleeve is withdrawn from the axial passage as the pusher tube is advanced through the natural body lumen.

8. A method as in claim 1, wherein the natural body lumen is selected from the group consisting of a urethra, a ureter, a blood vessel, a hepatic duct, a cystic duct, a cervical canal, and a fallopian tube.

9. A method for accessing a urinary tract, said method comprising:
   disposing an everted edge of a lubricious sleeve adjacent to an access point to a ureter; and
   distally advancing a pusher tube against a proximal side of the everted edge to distally advance the everted edge through the ureter and into the urinary tract, wherein an outer proximal end of the sleeve is immobilized relative to the pusher tube, and wherein a lumen tube is attached to an inner distal end of the sleeve and is drawn into the body lumen by the inner distal end of the sleeve.

10. A method as in claim 9, further comprising immobilizing the outer proximal end of the sleeve using a sheath tube secured to said outer proximal end and disposed through a urethra.

11. A method as in claim 9, further comprising introducing or removing a material or instrument through a lumen of the lumen tube.

12. A method as in claim 9, wherein the lubricious sleeve is positioned through a cannula passing through the urethra and into a bladder prior to advancing the pusher tube.

13. A method as in claim 12, wherein the cannula comprises an endoscope positioned to view the access point to the ureter.

14. A method as in claim 9, wherein the lubricious sleeve is initially disposed in an axial passage of the pusher tube and the pusher tube.

15. A method as in claim 14, wherein the lubricious sleeve is withdrawn from the axial passage as the pusher tube is advanced through the natural body lumen.

16. A method as in claim 9, wherein the everted edge is advanced into the upper urinary tract.

17. A method as in claim 9, wherein the everted edge is advanced into the kidney.

* * * * *